United States Patent
Yang et al.

(10) Patent No.: US 7,645,996 B2
(45) Date of Patent: Jan. 12, 2010

(54) MICROSCALE GAS DISCHARGE ION DETECTOR

(75) Inventors: Wei Yang, Minnetonka, MN (US); Ulrich Bonne, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 476 days.

(21) Appl. No.: 11/553,948

(22) Filed: Oct. 27, 2006

(65) Prior Publication Data

US 2008/0142715 A1   Jun. 19, 2008

(51) Int. Cl.
*G01T 1/29* (2006.01)
*H01L 21/30* (2006.01)

(52) U.S. Cl. ............ 250/370.1; 250/336.1; 250/339.02; 250/374

(58) Field of Classification Search ............... 250/336.1, 250/339.02, 370.1, 370.01, 374, 389, 393, 250/395, 488.1, 492.21, 492.3
See application file for complete search history.

(56) References Cited

U.S. PATENT DOCUMENTS

| | | | |
|---|---|---|---|
| 3,344,302 A | | 9/1967 | Engh et al. |
| 3,478,213 A | | 11/1969 | Simon et al. |
| 3,767,955 A | | 10/1973 | Johnson |
| 6,362,484 B1 * | | 3/2002 | Beyne et al. ............... 250/374 |
| 6,836,059 B2 | | 12/2004 | Smith |
| 6,847,036 B1 | | 1/2005 | Darling et al. |
| 7,019,446 B2 | | 3/2006 | Funsten et al. |
| 7,560,788 B2 * | | 7/2009 | Fortin et al. .................. 257/415 |
| 7,563,692 B2 * | | 7/2009 | Fortin et al. .................. 438/456 |
| 7,579,589 B2 * | | 8/2009 | Miller et al. ................. 250/292 |
| 2004/0206911 A1 | | 10/2004 | Laprade |
| 2006/0063354 A1 * | | 3/2006 | Fortin et al. .................. 438/459 |
| 2008/0142715 A1 * | | 6/2008 | Yang et al. ............... 250/336.1 |
| 2009/0151429 A1 * | | 6/2009 | Jun et al. .................... 73/31.06 |

FOREIGN PATENT DOCUMENTS

EP   1018647   7/2000

(Continued)

OTHER PUBLICATIONS

Osmokrovic et al., "The Influence of The Electric Field Shape on the Gas Breakdown Under Low Pressure and Small Inter-Electrode Gap Conditions", IEEE Trans. Plasma Scie. 33(5) 2005, 1677-1681).*

(Continued)

*Primary Examiner*—Bernard E Souw
(74) *Attorney, Agent, or Firm*—Kris T. Fredrick

(57) ABSTRACT

A microscale planar device for detecting particles under high pressure with high sensitivity. The device may have an anode and cathode with an insulator situated between them. The insulator may have a number of holes, cavities or channels between the anode and cathode. There may be conductive rings at the perimeters of openings of the channels on the anode side of the insulator. These rings may be a part of the anode. An ion may be attracted into one of the channels where it interacts with a gas to result in an avalanche breakdown. The breakdown may be detected by instrumentation connected to the anode and cathode. The lateral and/or longitudinal dimensions of the channels may be such that the device may operate as a detector with ambient air as a gas under its pressure of about one atmosphere.

21 Claims, 4 Drawing Sheets

FOREIGN PATENT DOCUMENTS

| | | |
|---|---|---|
| GB | 2409927 | 7/2005 |
| WO | 2005066620 | 7/2005 |

OTHER PUBLICATIONS

Schilling et al., "Simultaneous Multi-Elemental Analysis of Transient Signals Using a Faraday-strip Array Detector Coupled to a Mattauch-Herzog Mass Spectrograph," Paper No. 630-2, Pittcon, Orlando FL, 2 pp. Mar. 13, 2006 (Abstract).

Turner et al., "An optimized Faraday cage design for electron beam current measurements," Journal of Physics E. Scientific Instruments, Nov. 1975 (Abstract).

Darling et al., "Micromachined Faraday cup array using deep reactive ion etching," Sensors and Actuators, A 95, pp. 84-93, 2002.

* cited by examiner

MICROSCALE GAS DISCHARGE ION DETECTOR

BACKGROUND

The U.S. Government may have certain rights in the present invention.

The invention pertains to detectors and particularly to ion detectors. More particularly, the invention pertains to gas discharge ion detectors.

SUMMARY

The invention is a microscale gas discharge ion detector.

DESCRIPTION

Ion detectors may fall into several categories which include electron multipliers (e.g., Channeltrons™) and Faraday cage or cup detectors. Neither category is suitable for use in compact, portable and hand-held micro analyzers. Electron multipliers need a very low pressure, i.e., below the millitorr level, for proper operation with electron multiplication, which is incompatible with operation at about one atmospheric pressure. It appears difficult to incorporate ion detection in a microscale (e.g., wafer-like or MEMS) structure and maintain a good vacuum for the main components of the detector.

Faraday cup detectors, while operating at or near atmospheric pressure, do not provide intrinsic amplification of a multiplier, and thus have limited usefulness in high-sensitivity applications. Neither category is readily manufacturable at the wafer level to achieve compactness and low cost.

High sensitivity charged particle detection, which effectively requires single charge detection sensitivity, appears to have previously relied on electron multiplier tubes. These tubes require high vacuum and thus are not suitable for operation in the ambient high pressures of air. There may also be macro scale Geiger-Muller tubes as well as electron multipliers of various configurations which may be gas filled to about 0.1 atmosphere for charged particle or photon detection.

However, there is a strong interest in providing a miniature gas analyzer system working at ordinary atmospheric pressures, and using ambient air as a gas for discharge. Such system should include higher pressure operation of Faraday cup or cage detectors and higher sensitivity of electron multipliers.

Figure 1:
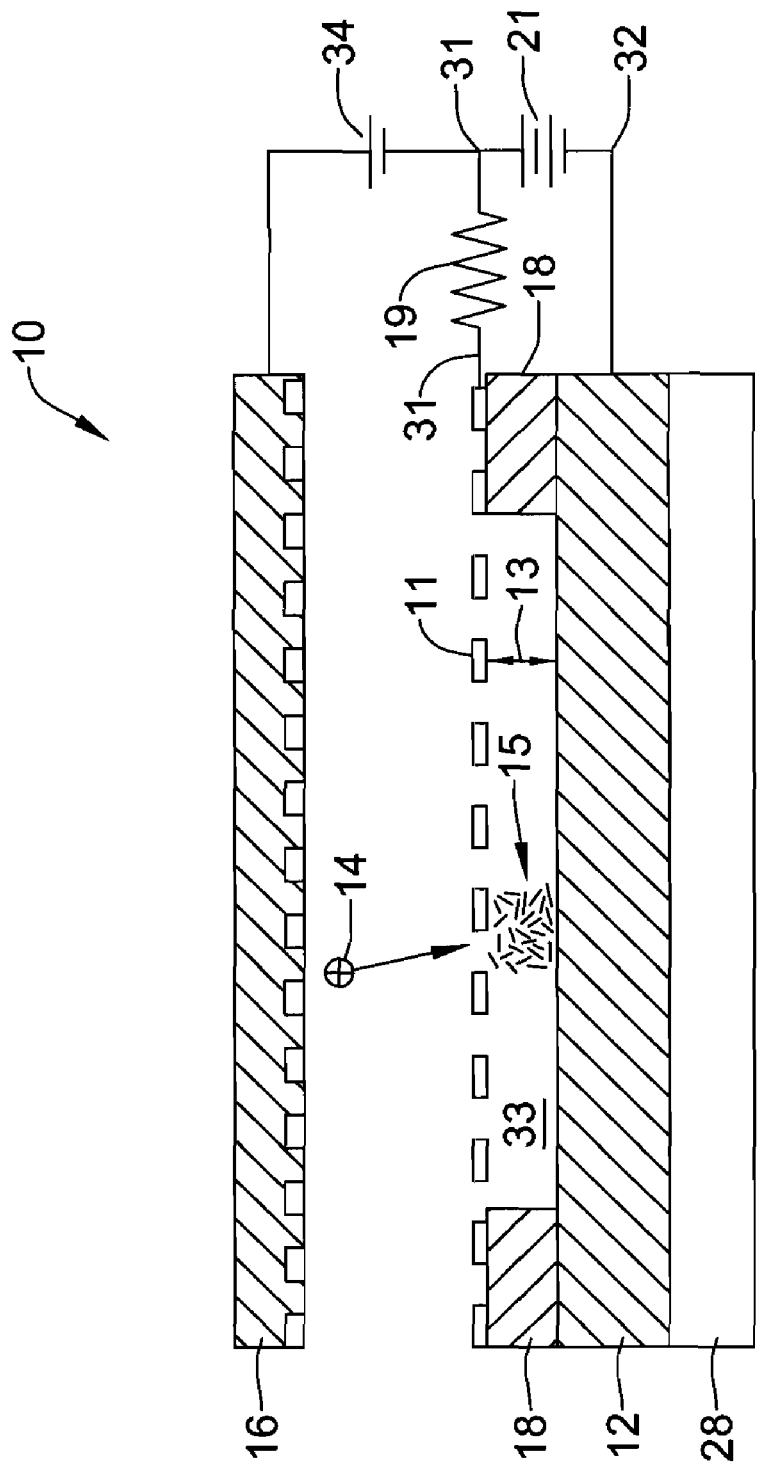
FIG. 1 is a schematic of a basic structure of a planar micro ion detector for operation at an atmospheric pressure.
Figure 3:
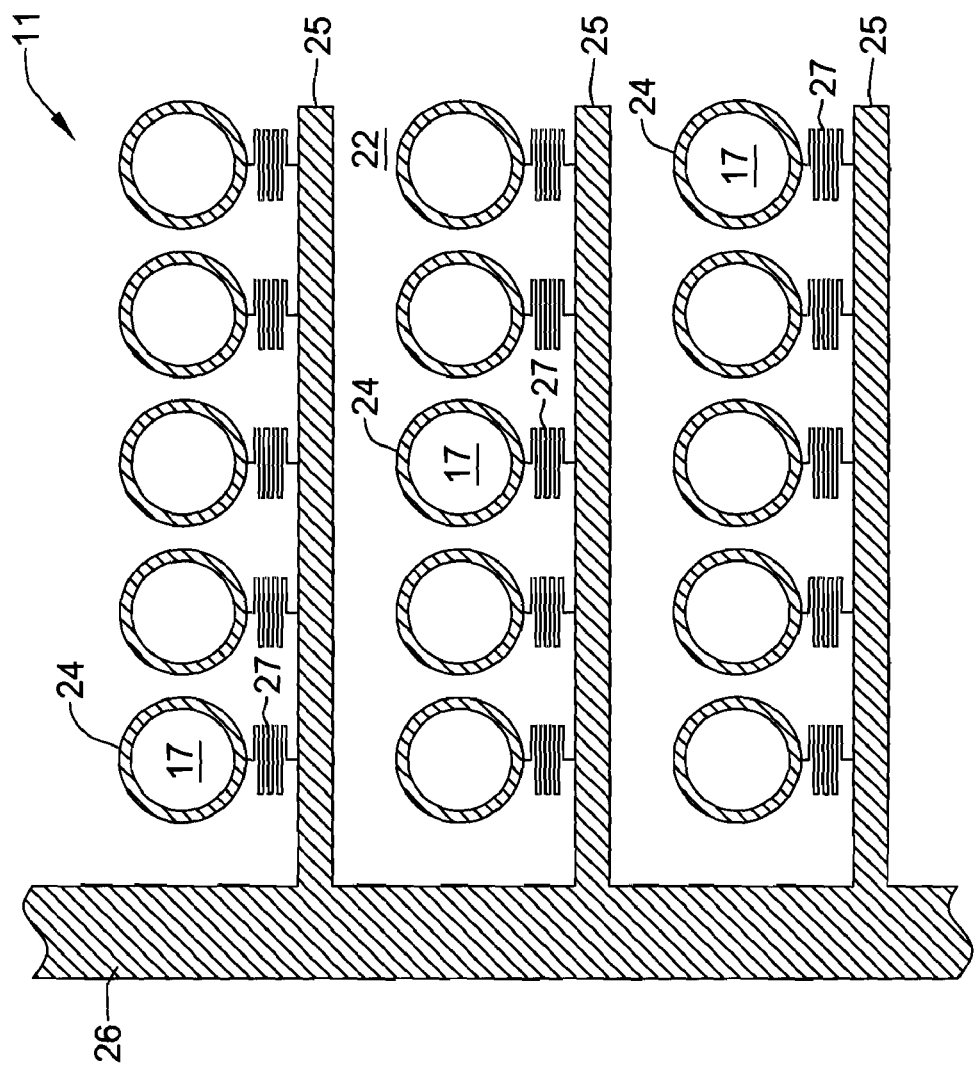
FIG. 3 is a plan view of anode components on an insulation layer.
Figure 4:
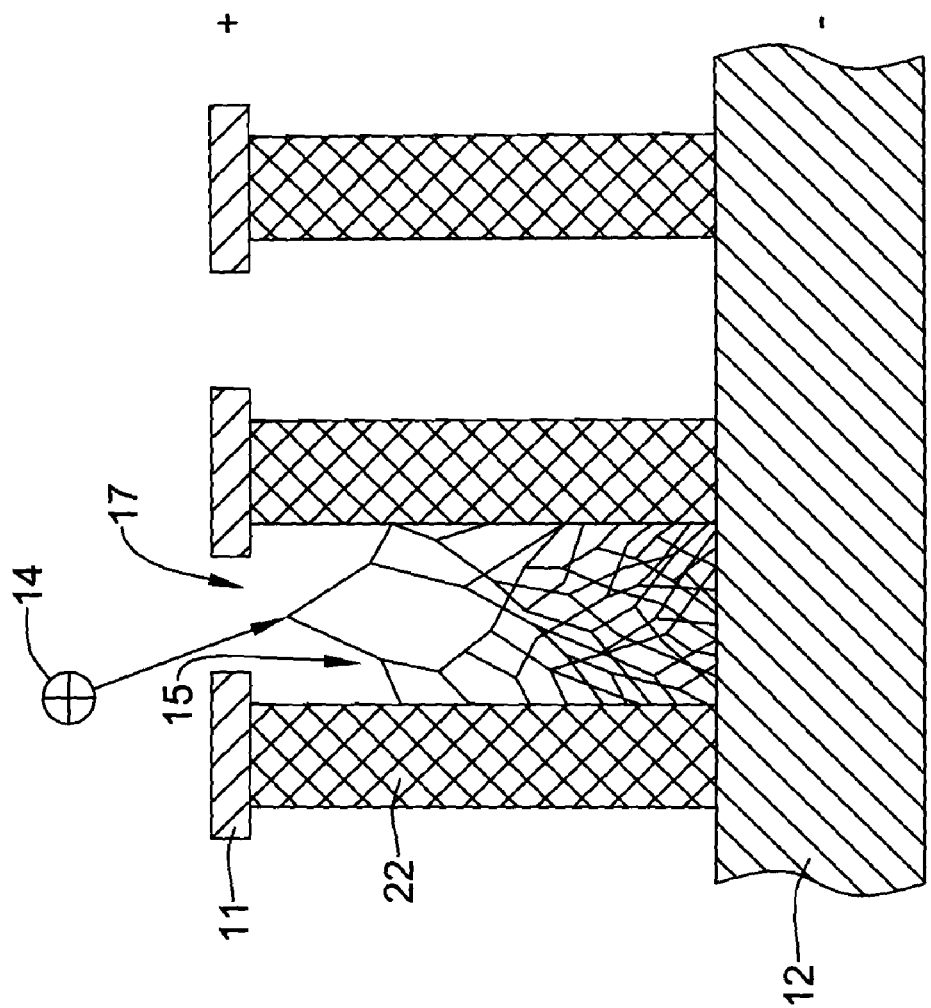
FIG. 4 is a schematic of the planar micro ion detector having confined discharge and surface quenching in a micro channel.

In FIG. 1, the device may have a planarized microscale structure. Device 10 may have a flat anode grid 11 supported by an insulating spacer 18 at the perimeter at a distance 13 from a cathode base plate 12. The cathode 12 may also be a thin film metal on a substrate 28. The electrodes 11 and 12 may be approximately parallel to each other and have a distance, region or gap 13 ranging from 10 microns to 500 microns, between them. In operation, about 400 to 800 volts from a voltage source 21 may be applied across the electrodes 11 and 12 via terminals 31 and 32, respectively, resulting in a high electric field in the region or gap 33. The voltage across the electrodes may be adjusted in response to ambient pressure and/or temperature changes relative to devices 10 and 20 (FIG. 3). The photosensitivity of detectors 10 and 20 may be minimized by coating one or more of the electrode surfaces with a high work function metal or fabricating one or more of the electrodes with a high work function metal.

Figure 2:
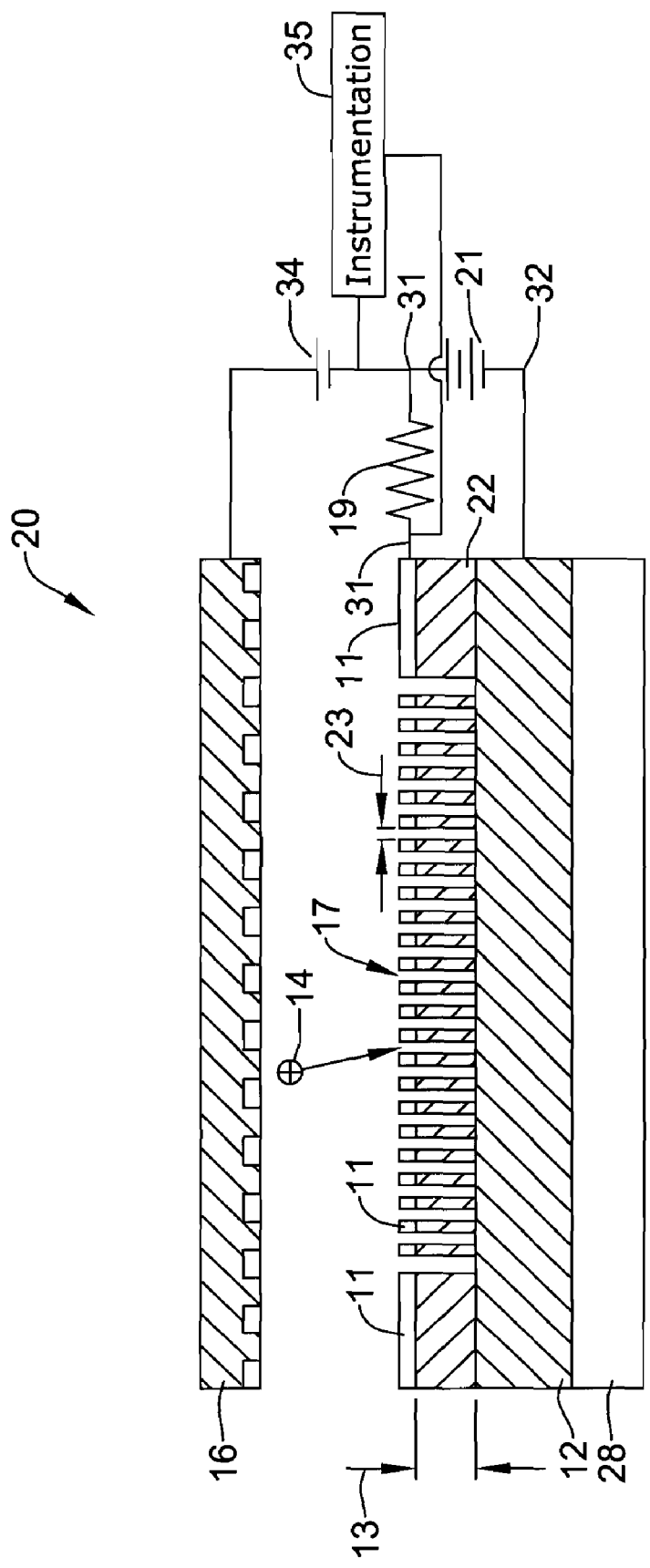
FIG. 2 is a schematic of the planar micro ion detector having a quenching enhancement.

FIG. 2 shows device 20 that is situated in a planarized microscale structure like that of device 10. However, instead of spacer 18, device 20 may have an insulator layer 22 that is situated effectively over the cathode 12 surface. Device 20 has other structural and operational characteristics that distinguish it from device 10. Situated in the insulator layer 22 may be holes, openings, channels or cavities 17 that go from one broad surface proximate to a terminal or anode 11 through the layer to the other broad surface of layer 22 proximate to cathode 12. The holes, channels or cavities 17 may be round or of any other shape. They may have a longitudinal dimension or length 13 between 10 microns and 500 microns. This dimension may be the same as the thickness 13 of the region or gap 33 of device 10. The holes, channels or cavities 17 may have a lateral dimension, width or diameter 23 between 0.5 micron and 25 microns. For a given detector 20, the holes, channels and cavities 17 may have similar magnitudes for the lateral dimensions 23 and longitudinal 13 dimensions, respectively.

The lateral dimension 23 may depend on the pressure of the gas in the cavity, hole or channel 17. The relationship may be inversely proportional. For instance, the lateral dimension 23 may be selected from one micron to 100 microns for a pressure range of 1000 torr to 10 torr, respectively. For a one atmosphere device, dimension 23 may be about 1.3 microns, depending on structural features of the device 20 and the kind of gas present.

The cross-section view of device or detector 20 in FIG. 2 shows cavities, holes or channels 17. They may appear as slots, but that appearance is because of the cross-section being through the centers of the cavities, holes or channels 17.

FIG. 3 is a top view showing holes 17 having a circular shape. These holes 17 may instead have a square, oval, or another shape. The spacing between the holes 17 may be of various distances and patterns. On layer 22 may be the electrode or an anode 11. The anode 11 shown in FIG. 3 is an illustrative example since other anode configurations and patterns may be used. Each cavity, channel or hole 17 may have a conductive material, strip, loop or ring 24 around the perimeter of it. Ring 24 of, for instance, each hole 17 may be connected to a main anode electrode (finger) 25 which may in turn be connected to another main anode electrode 26. The electrodes 25 and 26 are shown but there may be more such electrodes 25 and 26. The conductive rings 24, or the like, electrodes or conductors 25 and 26 may be a part of anode 11. The rings 24 and electrodes 25 and 26 may be composed of a low resistance conductive material such as, for example, a metal film greater than 0.01 micron thick. The anode 11 may initially cover the entire surface of insulative layer 22 and the like. Then a pattern of cavities, channels or holes 17 may be made through the anode 11 and layer 22. A combination of etching and deposition may result in a resistive component or element, or resistor 27 that is connected between the conductive ring 24 and electrode or conductor 25. Component, element or resistor 27 may for example be a thin film resistor (e.g., a serpentine line) 27 connecting each ring 24 of each hole or cavity 17 to the conductor or electrode 25. The resistor 27 may have a value between one and 1000 megohms. The resistive element or resistor 27 may be made of polysilicon, a metal nitride, thin metal film, or other material.

The cathode 12 may be a stable metal such as platinum or gold and, for instance, be deposited as a thin firm on a substrate 28. Insulative layer 22 may be made from glass, silicon dioxide, an oxidized surface, or the like. The channels, holes or cavities 17 may be made with RIE (reactive ion etch) or some other appropriate approach.

The particle or ion source for detector 20 may of various kinds, an example being a structure 16 having ion traps. Structure 16 may be connected to a positive terminal of a small voltage battery 34 which has a negative terminal connected to terminal 31. For example, positive ions 14 in the traps of structure 16 may then be attracted to anode 11 elements because of a negative voltage on anode 11 relative to the voltage on structure 16. Other polarity arrangements may be incorporated in detector or device 20 for other particles of negative or no charge.

Because of a high electric field between the electrodes 11 and 12 due to the voltage across the electrodes, a gas within the region of hole 17 may be capable of avalanching, if initiated, even at ordinary atmospheric levels of ambient pressure. The avalanching discharge 15 is a process of attaining more ions through collisions between a first-generation of ions, which are sufficiently energized by the applied electric potential during the time between ion-neutral collisions, to knock out electrons off the neutral atoms or molecules resulting in more ions. Thus, when an ion 14 passes through the anode grid and enters the high electric field region 13, it may be accelerated by the electric field and initiate an avalanche breakdown or discharge 15. A current pulse associated with this breakdown may be detected with appropriate circuitry and instrumentation. For instance, a resistor 19 in series with terminal 31 may be monitored with a voltmeter and/or other instrumentation 35 connected across the resistor to detect or measure changes in voltage drop caused by current pulses through the resistor, and measure counts, amplitudes of them, and other parameters for computation and/or processing. Resistor 19 may also be a safety resistor for limiting current to prevent damaging the detector. An example value of resistor 19 may be about 100K ohms. For instance, a current pulse measured in resistor 19 may be regarded as a counted particle.

The device 20 may have a design to provide fast quenching thus have a high count rate. As shown in FIG. 2, vertical cavities, holes or channels 17 etched into an insulating layer 18 between the anode and cathode, may serve to confine the discharge in a localized site, e.g., a single channel 17. The cavity, channel or hole 17 may also increase the probability of excited gas molecules to lose energy by interaction with the wall. This characteristic may help reduce the quench time and increase the count rate.

The quenching may be facilitated with a resistor 27 between the ring 24 and terminal 31. However, the resistor might not be needed since the discharge substantially relies on surface collisions and ionization of adsorbed molecules, and once the molecules are desorbed or ionized and flushed out of the channel, the discharge may quench by itself.

When one puts a micro cavity, hole or channel 17 in the device 20 (FIG. 2), a pixel-discharge may be confined within the micro channel 17 (unlike the conventional tubes where the discharge flares out). The discharge may merely render that channel 17 inactive for a short time (i.e., about 10 μsecs). However, there may be plenty of other channels 17 in a ready state for particle detection. Therefore, a temporarily disabled channel 17 may not cause any count to be missed after all. The bottom line is that one may obtain a high count rate without reading or externally quenching individual channels 17. One may just apply a constant voltage and count the current pulses. Each current pulse may be much smaller in magnitude (e.g., 10 nA versus mA in large tubes), but one may count many more pulses with the smaller device 20. If one has many channels 17, then the count may be so fine that one may actually obtain analog output similar to an electron multiplier tube. The dynamic range of detector 20 may be six orders of magnitude.

A large number of the devices or detectors 20 may be built on a wafer, and when working in parallel, they can achieve a much higher count rate than one discrete detector. Using a wafer fabrication process for building the detector may also lead to low manufacturing costs. Additionally, connecting individual "pixels" (i.e., detectors 20) to separate voltage supplies and load impedances may enable an overall detector to achieve a wider dynamic range than conventional Geiger tubes.

The detector 20 may be best utilized in applications, which need high sensitivity ion detection near or at atmospheric pressures. The microscale and planar configuration of the detector 20 may enable operation at higher pressure. A strong surface interaction within a channel 17 may contribute to a much higher count rate. The detector 20 may be a MEMS (micro electro mechanical systems) device constructed with MEMS fabrication technology that is integratable with other MEMS structures such as micro gas analyzers. Due to its planar structure, the detector 20 may be integratable with a planar ion source, such as an ion trap mass spectrometer (ITMS). The detector 20 may be integratable with other MEMS, wafer and microscale planar devices such as gas analyzers. This integratable characteristic may permit device 20 to have application in portable gas sensing and other like instrumentation.

Such a system may enhance specificity and sensitivity when working in conjunction with a micro ion trap mass spectrometer (ITMS). The ITMS sensitivity may in part be determined by the characteristics of an associated ion detector, which also would need to operate at near or at atmospheric pressure. The detector 20 may fulfill that requirement. The present ion detector may be based on a gas discharge at a microscale level, which may meet the needs for both high pressure (i.e., about one atmosphere) operation and good sensitivity.

The ion detector 20 may be based on gas discharge in a microscale structure, which provides a solution to meet the needs of both high-pressure operation and good sensitivity within ambient air. The present detector may be realized in a planarized microscale structure designed for operation under approximately one atmosphere pressure. As to a principle of the detector 20, the detector may use micro gas discharge and surface quenching to achieve single charge (electron or ion) detection sensitivity and a very high count rate. Detector 20 may have a strong surface interaction and homogeneous ion production as part of the avalanche formation and subsequent quenching which contributes to the very high count rate.

It may be noted that the optimal bias voltage of a Geiger tube is a function of the gas density. Therefore, when the detector is operated in ambient gas, unlike sealed tubes, it may require external means to regulate the gas density, or adjust bias voltage in response to ambient condition changes, such as pressure and temperature.

One may note the interdependence of electrode shape and size, the gap distance, the operating voltage, the operating pressure, and so on. Examples of such parameters may involve the breakdown potential as governed by the p*d, product (p=pressure, d=electrode gap), the E/p value (E=voltage), the discharge regions, and so on.

The gas pressure, gap distance and operating voltage are governed by Paschen's law that gives the relationship between the breakdown voltage ($V_b$) and the pressure-gap distance product (p*d) for a specific gas which may be in the form of what is known as the Paschen curve. Therefore, the operating voltage of the described detector can be estimated based on the gas pressure and electrode gap using the Paschen curve applicable to the specific gas used for the device. The operating voltage should be slightly below, but sufficiently close to the breakdown voltage given by the Paschen curve, thus preventing the device from continuous discharging while maintaining high sensitivity. Paschen's law is known from related-art textbooks and literature. For example, one may review "Electric Breakdown of Gasses," by J. M Meek and J. D. Craggs, Oxford, 1953.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A particle detector comprising:
   a substrate;
   a conductive layer situated on the substrate;
   an insulative layer situated on the conductive layer;
   a plurality of openings situated through the insulative layer; and
   a conductive material on the insulative layer without covering the respective opening; and
   wherein:
   the plurality of openings are situated in air being at one atmosphere of pressure;
   each opening has a lateral dimension between 0.5 micron and 25 microns; and
   each opening has a longitudinal dimension between 10 microns and 500 microns.

2. The detector of claim 1, wherein
   the conductive material on the insulative layer without covering the respective opening of the plurality of openings is connected to a first terminal; and
   the conductive layer is connected to a second terminal.

3. The detector of claim 2, wherein:
   the first terminal is for connection to a first polarity of a voltage source; and
   the second terminal is for connection to a second polarity of the voltage source.

4. The detector of claim 2, further comprising a resistive component connected between each conductive material on the insulative layer without covering the respective opening of the plurality of openings and the first terminal.

5. The detector of claim 4, wherein each resistive component has a value between one megohm and 1000 megohms.

6. The detector of claim 1, further comprising a plurality of ion traps situated in a structure proximate to the conductive material on the insulative layer without covering the respective opening of the plurality of openings.

7. A particle detection system comprising:
   a cathode layer;
   an insulating layer having a first surface situated on the cathode layer and having a second surface approximately parallel to the first surface; and
   an anode situated on the second surface of the insulating layer; and
   wherein:
   the insulating layer comprises a plurality of cavities;
   each cavity of the plurality of cavities has an opening at the second surface of the insulating layer;
   the anode comprises a plurality of conductive loops around the openings; and
   each cavity of the plurality of cavities has a diameter dimension commensurate with operation at one atmosphere of pressure.

8. The system of claim 7, wherein the diameter dimension of each cavity is between 0.5 micron and 10 microns.

9. The system of claim 7, further comprising:
   a terminal; and
   wherein:
   each conductive loop of the anode is connected to a resistive element; and
   each resistive element is connected to the terminal.

10. The system of claim 9, wherein each resistive element has a resistance between one megohm and 1000 megohms.

11. The system of claim 7, further comprising an ion trap structure proximate to the anode.

12. The system of claim 7, wherein the plurality of cavities is situated in air.

13. The system of claim 7, wherein the cathode layer, the insulating layer and the anode are fabricated with MEMS technology.

14. A method for detecting particles comprising:
   providing an insulative layer;
   making one or more holes having a certain diameter through the insulative layer;
   placing a first electrode on a first side of the insulative layer;
   placing a second electrode on a second side of the insulative layer; and
   connecting the first electrode and the second electrode to a voltage source, making one or more holes having a certain diameter through the insulative layer and through the first electrode layer; and
   wherein:
   an ion passing through an opening in the first electrode into one or more holes of the insulative layer and accelerating toward the second electrode initiates an avalanche breakdown of a gas in the hole; and
   the certain hole diameter having a magnitude so that the avalanche breakdown may occur under a particular pressure of gas.

15. The method of claim 14, wherein the pressure of the gas is one atmosphere.

16. The method of claim 14, wherein the gas is air.

17. The method of claim 14, wherein the insulative layer and electrodes are fabricated with MEMS technology.

18. A system for detecting particles comprising:
   a cathode;
   an insulator layer on the cathode, the insulator comprising one or more channels; and
   an anode layer on the insulator; and
   wherein:
   each channel of the one or more channels comprises an opening, and a conductor around the opening;
   the conductor around the opening serves as an anode;
   if a certain voltage is applied across the anode and the cathode, and an ion enters a channel of the one or more channels, the ion may be accelerated and initiate an avalanche breakdown of a gas in the channel;
   the certain voltage may be adjusted in response to pressure;
   the avalanche breakdown causes a pulse across the anode and cathode; and
   the pulse indicates an ion count.

19. The system of claim 18, wherein each of the one or more channels has a length from the opening through the insulator towards the cathode.

20. The system of claim 18, wherein:
   each of the one or more channels has a lateral dimension between 0.5 micron and 25 microns; and
   each of the one or more channels has a length between 10 microns and 500 microns.

21. The system of claim 18, wherein the photosensitivity of the system may be minimized by coating the surface of the anode and/or the cathode with a high work function metal or fabricating the anode and/or the cathode with a high work function metal.

* * * * *

UNITED STATES PATENT AND TRADEMARK OFFICE
CERTIFICATE OF CORRECTION

PATENT NO. : 7,645,996 B2
APPLICATION NO. : 11/553948
DATED : January 12, 2010
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 553 days.

Signed and Sealed this

Sixteenth Day of November, 2010

David J. Kappos
*Director of the United States Patent and Trademark Office*